United States Patent [19]

Dracker

[11] Patent Number: 5,356,373
[45] Date of Patent: Oct. 18, 1994

[54] METHOD AND APPARATUS FOR AUTOLOGOUS TRANSFUSIONS IN PREMATURE INFANTS

[75] Inventor: Robert A. Dracker, North Syracuse, N.Y.

[73] Assignee: Miles Inc., Berkeley, Calif.

[21] Appl. No.: 792,824

[22] Filed: Nov. 15, 1991

[51] Int. Cl.⁵ ............................................. A61M 37/00
[52] U.S. Cl. .......................................... 604/4; 604/317
[58] Field of Search .................................. 604/4–6, 604/410, 416, 317–321; 128/762

[56] References Cited

U.S. PATENT DOCUMENTS

| | | | |
|---|---|---|---|
| 4,457,747 | 7/1984 | Tu | 604/4 |
| 4,846,806 | 7/1989 | Wigness et al. | 604/175 |
| 4,865,583 | 9/1989 | Tu | 604/53 |
| 5,053,025 | 10/1991 | Knippscheer | 604/317 |
| 5,059,168 | 10/1991 | Stone | 604/4 |
| 5,084,034 | 1/1992 | Zanotti | 604/319 |
| 5,097,842 | 3/1992 | Bonn | 128/762 |

Primary Examiner—Robert A. Hafer
Assistant Examiner—Sam Rimeu
Attorney, Agent, or Firm—Elizabeth F. Enayati; James A. Giblin

[57] ABSTRACT

Method and apparatus for collecting and storing umbilical blood in a system that allows for the closed aliquoting of small blood volumes for autologous transfusion in neonates. The method involves locating a venous access site on an umbilical cord of the placenta of a neonate. A vacuum pressure is applied to a blood collection bag to facilitate removal of an amount of blood from the umbilical cord. The blood may then be stored in the collection bag and used for subsequent autologous neonate blood transfusion.

7 Claims, 3 Drawing Sheets

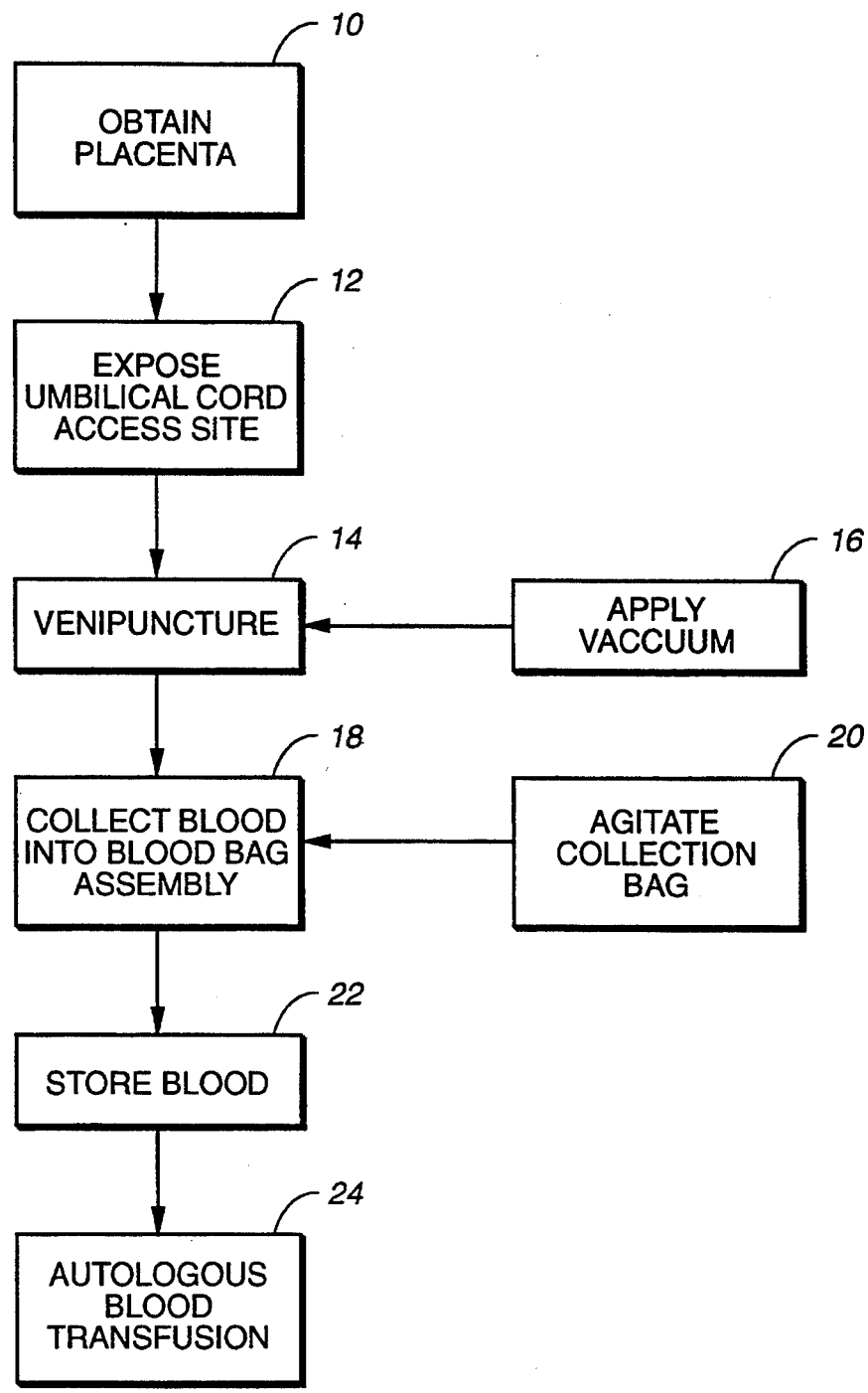
FIG._1

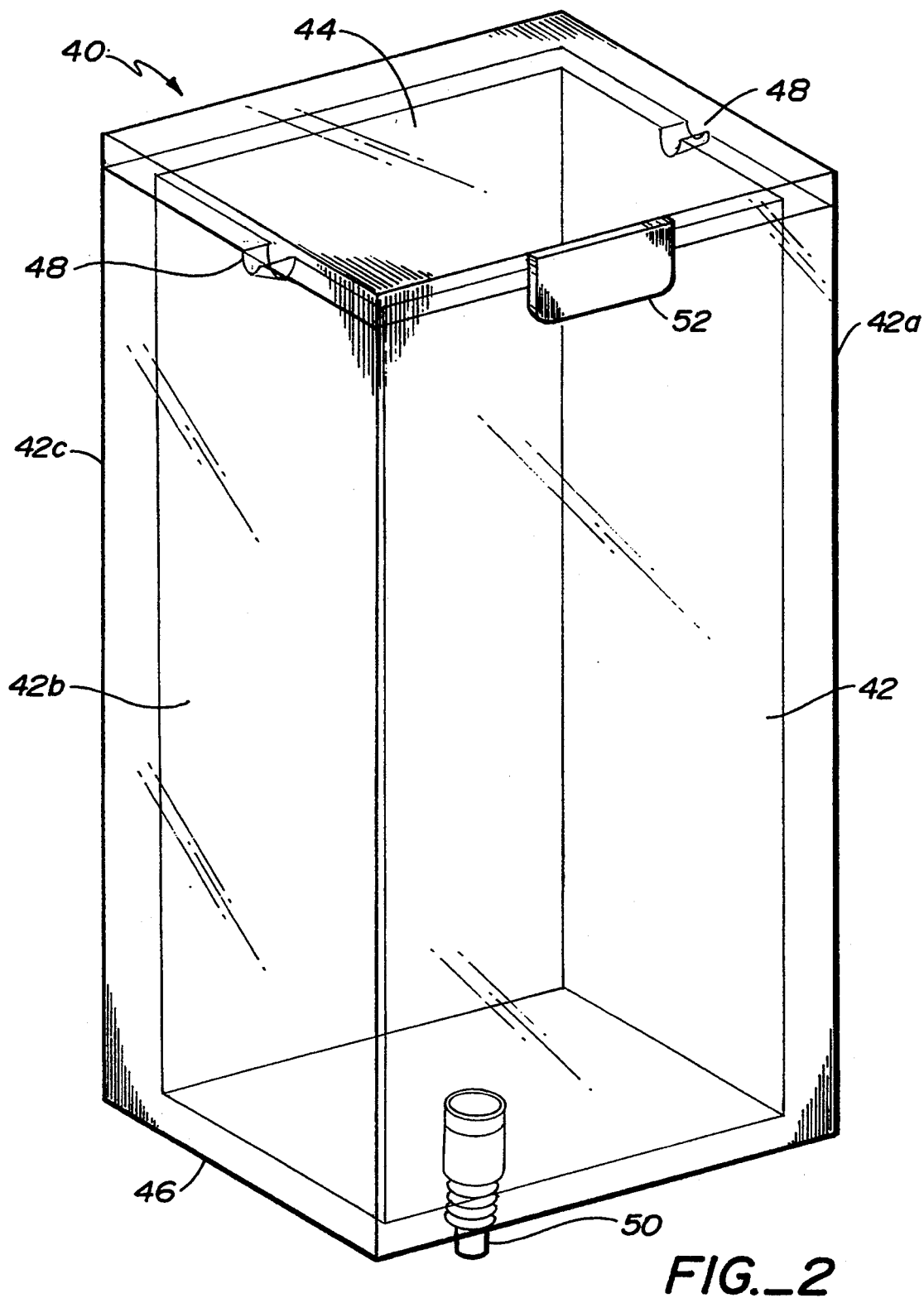
FIG._2

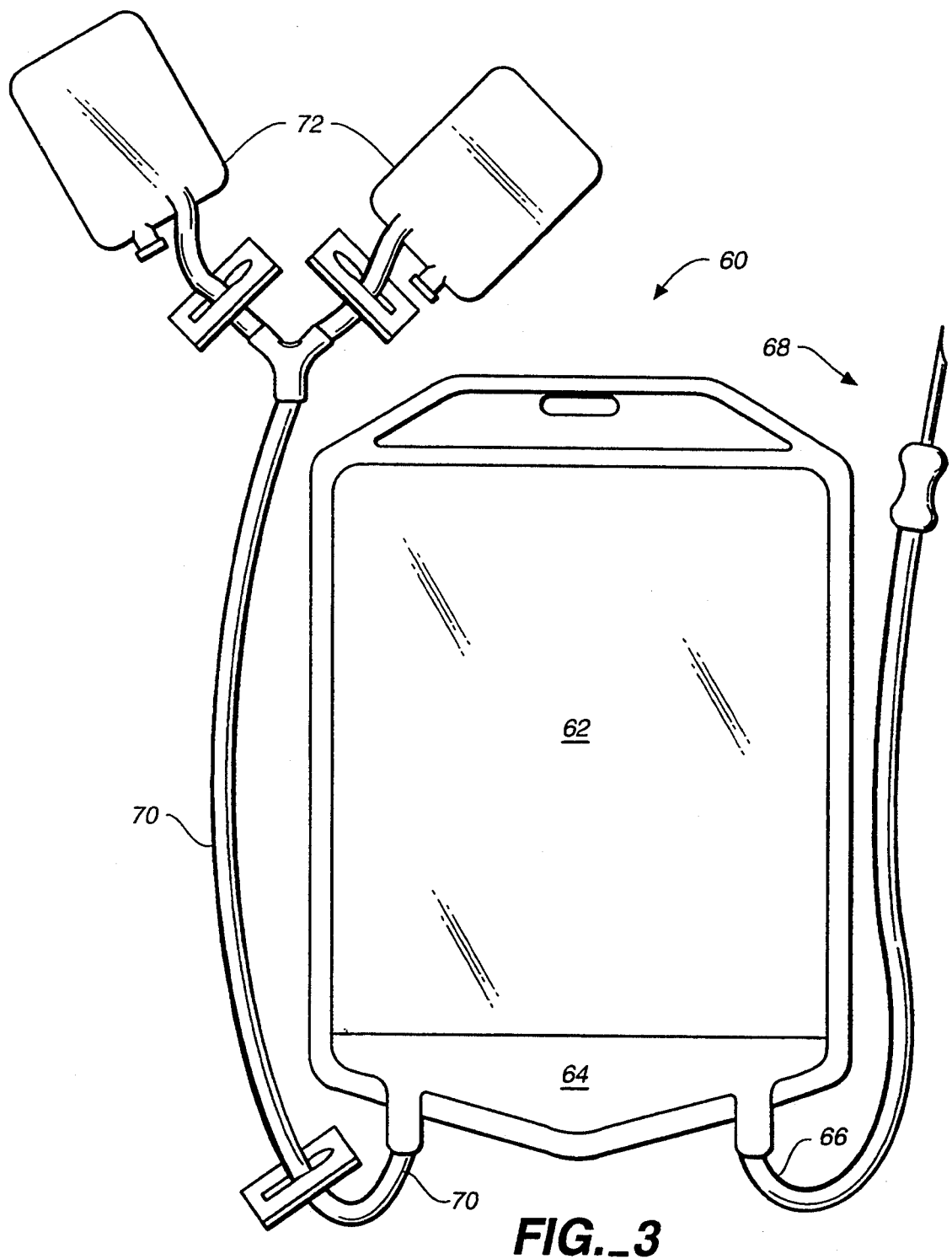
FIG._3

METHOD AND APPARATUS FOR AUTOLOGOUS TRANSFUSIONS IN PREMATURE INFANTS

BACKGROUND

In the United States, over 40,000 very low birth weight (VLBW) infants are born each year, many of whom are critically ill and require care in neonatal intensive care facilities. Invariably, most infants of less than 1,500 grams receive blood transfusions. The use of red cell transfusion is an invaluable part of the care for these infants. Such transfusions are particularly needed for exchange transfusions in treating either hemolytic disease of the newborn or hyperbilirubinemia. More commonly, such transfusions are for treating anemia due to physiologic changes and routine phlebotomy, since such procedures often impair already suppressed cardiorespiratory function.

Most very low birth weight (VLBW) infants receive red blood cell transfusions during the first four weeks of life. A recent study revealed that in 22 transfused neonates, each received an average of 2.5 homologous CPDA-1 RBC transfusions (range 1 to 11), having a mean volume of 16 ml and received a mean total transfusion volume of 60 ml. Transfusions are administered primarily to replace losses due to diagnostic sampling. The need for frequent monitoring of blood gasses and electrolytes, the small blood volumes of these infants (100/kg), and limitation on total volume administered at one time (10 cc/kg/transfusion), result in repeated exposure of these infants to the risks of homologous red blood cell transfusions. Results of another study indicate that an average homologous blood exposure rate of 6.9 (range 1 to 25) different donors in 52 neonatal intensive care unit infants. Seventy percent of infants present in their unit received transfusions during the study period.

In a recent study conducted at State University of New York at Syracuse, in the neonatal intensive care unit, 55% of VLBW infants born during a one-year period received a red cell transfusion; of these 86% experienced at least three transfusion episodes during the first month of life. Studies evaluating the rate of homologous blood donor exposures in neonates have documented exposure ranges of 2.4 to 10 different source exposures per neonate. The benefits of autologous transfusion in the adult population have been demonstrated, minimizing the risks of transfusion transmitted diseases associated with the homologous blood supply. These risks, including those associated with CMV infection, are of critical concern in the ill, premature neonate.

The placenta, usually discarded after birth, contains a reservoir of the infant's own blood representing an ideal source of autologous blood. Over the past ten years a few centers have used autologous blood obtained from placentas, transfusing the blood immediately following birth to volume-resuscitate newborns. Prior studies have documented the bacteriologic safety and proof of anticoagulation of placental blood harvested in heparinized containers. However, there are no known studies examining the safety and practicality of the extended storage of autologous placental blood for use in infants during the first month of life.

Although many blood banking techniques and approaches specifically addressing the needs of the small infant have been developed, most concerns are related to the handling of small blood volumes, minimizing donor blood wastage, and avoiding obvious risks of homologous blood exposure such as CMV transmission and graft versus host disease. Although the use of quadruple or "cow" packs allow for multiple transfusions from a single unit, this does not satisfactorily solve the problem of multiple donor exposures during the week to month long period of the infant's transfusion dependency.

Other suggested methods of minimizing infant exposure to multiple blood donors include the concept of the "walking donor" in which small volumes of blood are withdrawn from a donor as needed by the infant, frozen rbc aliquots from a single unit to be used by a designated infant, and creative uses of a sterile docking devise which would allow for the aseptic "closed" removal of blood aliquots from a donor unit, thereby maintaining the storage period and availability of the unit. To date, none of these concepts have proven practical for use in the transfusion dependent neonate. Although the treatment of neonatal anemia with recombinant erythropoietin would appear promising, several small studies evaluating this approach have shown little success.

Autologous fetal blood collected from the placenta has been used for volume resuscitation of the newborn in the delivery room for over ten years. Various studies have demonstrated that placental blood can be collected and adequately anticoagulated into heparinized containers for use within the first 12 hours of life. If transfused immediately, the autologous blood has been shown to have minimal bacteriologic risks. To date, there have been no studies evaluating the safety and practicality of collecting and storing placental blood for subsequent autologous transfusion during the first month of life. There is also little data on the hematologic and biochemical changes of fetal blood stored in CPDA-1 preservative banking placental blood by studying a new method of collection, and evaluating the bacteriologic safety, the adequacy of anticoagulation and the conditions for maintaining optimal red cell viability during storage.

SUMMARY

A method and apparatus for aseptically collecting and storing umbilical blood for up to 28 days at 4° C. in a system that allows for the closed aliquoting of small blood volumes for autologous transfusion in neonates. The inventive system also allows for the further characterization of fetal cells stored in preservative solutions.

The inventive method involves removing blood from the umbilical cord of a neonate, storing the blood, and subsequently transfusing the autologous blood to the neonate. In practicing the inventive method, the placenta associated with the neonate at birth is obtained, and the umbilical cord venous access site is exposed. Venipuncture is then performed at the venous access site using a catheter assembly.

Preferably, the catheter assembly is in communication with a blood collection bag, and/or a blood bag assembly. The blood collection bag may include a preselected amount of an anticoagulant, and other materials for preservation and subsequent use of the blood product collected therein.

The inventive method further includes the application of a vacuum in an amount sufficient to facilitate extraction of the blood. The vacuum may be applied in a manner consistent with blood cell viability, and in an amount sufficient to provide adequate blood draw with minimum damage to the blood product. In a preferred form of the inventive method, the vacuum is applied at a negative pressure of between about 5 mm Hg and 40 mm Hg.

The inventive method may also include the further step of periodically agitating, or lightly continuously agitating the collection bag and/or the blood bag assembly during blood collection. The periodic agitation may occur while the vacuum is being applied, or following collection to ensure sufficient contact of the collected blood product with any anticoagulant and other similar materials preloaded into the collection bag. Generally, the inventive method is performed using a closed blood bag system.

The invention further includes an assembly for collecting blood from a placenta for autologous neonate blood transfusion. The apparatus, or assembly, includes a substantially hollow box having a hinged sealable top panel, suction means integral with a bottom panel for applying a vacuum suction to the interior of the box, and a plurality of tube ports. The tube ports are preferably integral with the top panel, however, they may be positioned in other locations about the box depending upon the specific application for the assembly.

The interior portion of the box is of a size and shape sufficient to hold a blood bag collection system of the type having at least one blood collection bag and optionally including various satellite and/or auxiliary bags. The blood collection bag may include an anticoagulant, while the satellite bags may contain reagents such as a blood cell storage solution, an anticoagulant, a preservative, or a saline solution.

The blood bag system generally includes a tubing system connecting the various blood bags in the box to the collection point. One end of the tubing leading to the blood collection bag generally includes a sterile needle of preselected gauge. The tubing thus extends from the collection point, or needle, through the tubing, through the tubing ports in the box, and into the blood collection bag contained within the box.

The blood collection bag is generally flexible to enable it to respond to the vacuum suction as it is applied in the box and thus on the collection bag. Once the vacuum is established within the box, the flexible blood bag expands outwardly creating a negative pressure within the bag. This negative pressure is transmitted through the connected tubing and the attached terminal needle. During operation of the inventive method, the needle is inserted into the umbilical cord at a preselected access site and blood is drawn through the needle into the collection bag. The drawing effect is achieved by the vacuum created within the box.

BRIEF DESCRIPTION OF THE FIGURES

FIG. 1 is a flow chart showing the steps involved in practicing the inventive method.

FIG. 2 shows a perspective view of the inventive blood collection assembly.

FIG. 3 shows a front plan view of a blood bag system that may form part of the inventive blood collection assembly.

Like elements in each FIGURE have the same reference number.

DESCRIPTION OF THE INVENTION

The amount of blood required by a neonate during the first month of life averages between 50 to 60 cc, depending on the size and illness of the infant. The collection of residual post partum umbilical-placental blood as obtained by practicing the present claimed invention results in sufficient amounts of autologous blood for most transfusion needs during at least the first two weeks of neonate life. Such a system may be used as a source of transplantable hematopoietic stem cells for the neonate. In addition, the collected blood sample may be subject to long-term cryopreservation.

Referring now to FIG. 1, the inventive method involves a series of steps directed to aseptically removing an amount of blood from the placenta, via the attached umbilical cord, of a neonate, storing the blood, and subsequently using that blood as material for a blood transfusion. Specifically, the first step of the inventive method involves obtaining the placenta 10 of the subject neonate. This must be performed by the physician or technician present at the birth of the neonate substantially at the time of birth. There is some degradation of blood product that occurs if there is delay in obtaining the placenta and umbilical cord. In some embodiments of the inventive method, it may be possible to preserve the placenta in a saline solution or the like for subsequent performance of the remaining inventive steps.

Once the placenta is obtained 10, the umbilical cord access site is exposed 12. Although it may be possible to access an artery, practical considerations such as size and direction of blood flow make venous access preferable over arterial access. However, arterial access is contemplated as being within the scope of the present inventive method.

Next, venipuncture 14 is performed at the exposed venous access site. This is achieved via a needle of an appropriate gauge, typically 16G. In a preferred form of practicing the inventive method, the needle is part of a catheter assembly connected to or integral with a blood bag collection system of the type described in further detail below. Such blood bag collection systems are generally commercially available from Cutter Biological, Miles Inc., Berkeley, California. Briefly, such systems include a blood collection bag containing an amount of an anticoagulant, various satellite or auxiliary bags, and a tubing network interconnecting the bags and enabling introduction of blood samples into the collection bag.

An important aspect of the present invention is the use of a flexible collection bag attached to the needle. Such a flexible bag is expandable upon application of pressure. Thus, in performing the next step of the present invention, applying a vacuum to the collection bag 16, the collection bag will expand in response to the vacuum, thus creating a suction through the needle that draws blood from the umbilical cord via the venipuncture site and into the collection bag.

The amount of vacuum applied depends upon a variety of variables readily determinable by one skilled in the art of blood collection. Specifically, variables such as neonate weight, size of the blood collection bag, needle gauge, and the like will affect the optimum amount of vacuum to be applied. In a preferred form of the inventive method, the amount of vacuum is applied at a negative pressure in the range of between about 5 mm Hg and about 40 mm Hg (i.e., −5 mm Hg and −40 mm Hg).

In one form of the inventive method, the collection bag is periodically and intermittently agitated during application of the vacuum 16. Thus, as the blood is collected into the blood bag assembly 18, the entire assembly or the collection bag only is periodically agitated 20. Alternatively, the collection bag may be continuously and gently agitated during collection 18. This agitation assists in dispersing the collected blood with any anticoagulant in the collection bag. If the collected blood does not evenly disperse with the anticoagulant, clumping of the collected blood may occur, which would seriously impair the viability of the collected blood.

Upon completion of collection of the blood 18 from the umbilical cord, the entire blood bag system may be stored for an amount of time 22. In a preferred form of the invention, the collected blood is stored for up to 28 days at 4° C. The specific amount of time the collected blood can be stored will depend upon several variables, such as temperature, amount, type of anticoagulant, and the like. These variables and the specific amount of time is readily discernible by one skilled in the art without undue experimentation. The storage temperature may also be varied in a similar manner.

In the preferred form of practicing the inventive system, the blood bag system is a closed system that permits sterile sampling of small blood volumes for performing autologous transfusion 24 of the collected blood. In a blood bag system have a plurality of auxiliary sampling bags, aliquots of blood may be transferred out of the collection bag without disturbing the integrity or sterility of the primary sample.

Further, each auxiliary or satellite bag may contain a predetermined amount of a reagent or preservative solution. In this manner, the fetal cells collected using the present inventive method may be characterized and analyzed following storage. The specific preservative solution or reagent contained in the satellite bags will depend upon variables such as the anticipated length of storage of the cells, the type of characterization tests anticipated, the specific subsequent use of the cells, and the like. These variables may readily be determined by one skilled in the art.

Turning now to FIG. 2, the present invention further includes an apparatus 40 for collecting blood from a placenta for autologous neonate blood transfusion. In a preferred form of the invention, the inventive apparatus 40 is used in practicing the inventive method described above.

Generally, the apparatus 40 includes a box having four integral or connected side walls 42a, 42b, back wall 42c, front wall 42d, a top 44 and a bottom 46. These elements are connected to form a box 40, and are preferably constructed of a material that can withstand the application of vacuum pressure (approximately between about −5 mm Hg and −30 mm Hg). A preferred material is a clear acrylic of the type generally commercially available in various forms.

In a preferred embodiment of the invention, the walls are approximately ¼ inch thick. The side walls 42a, 42b are approximately 7.25 inches high, and approximately 2.5 inches wide. The front wall 42c and back wall 42d are approximately 7.25 inches high and approximately 4.5 inches wide. These dimensions are exemplary and other dimensions may be used depending on variables such as the size and type of the blood bag collection system, the availability of materials, manufacturing and cost considerations, and the like.

The top panel 44 may be constructed using the same or similar material as the walls 42a–42d. In the illustrated embodiment of FIG. 2, the top panel 44 is hinged to the top portion of the front wall 42d, although it may alternatively be hinged to the top portion of any of the walls 42a–42d. The hinge is of the type generally commercially available, and is generally constructed to withstand the application of a vacuum, as described above.

The top panel 44 further includes at least one port 48 to permit passage of tubing between the inner portion of the box 40 to outside the box. The port 48 is generally inwardly angled to prevent tubing from bending or otherwise becoming deformed as it enters the box 40. The top may further include a latch 52 to maintain the box 40 in a closed configuration during blood collection.

In the illustrated embodiment, the bottom panel 46 includes a vacuum fitting 50 of the type generally commercially available. The vacuum fitting 50 includes a pipe tap with a main hose fitting extending from the box 40 to a vacuum source (not shown). The fitting 50 is preferably constructed of a polyethylene material, though other suitable materials are contemplated as being within the scope of the present invention.

FIG. 3 shows an exemplary blood bag system 60 that may be used in practicing the present invention. That system 60 includes a blood collection bag 62 for collecting approximately 75–150 ml of umbilical cord blood. The collection bag 62 may include a predetermined amount of anticoagulant solution 64, such as CPDA, that is pre-loaded prior to collection of the blood into the bag. The collection bag 62 is attached to a tube 66 that is open at one end into the collection bag 62 and has a needle 68 at the other end used for venipuncture at the access site of the umbilical cord.

The collection bag also includes an attached tube 70 that extends from the collection bag to one or more auxiliary bags 72. These auxiliary bags 72 may include a plurality of sampling bags, which are used to draw small blood samples for subsequent use without potentially contaminating the entire collected blood sample. The auxiliary bags 72 may be storage bags having different reagents or storage solutions. Blood samples may also be removed from the collection bag 62 into one or more of the auxiliary bags 72 for further characterization of fetal cells stored in preselected preservative solutions.

In a preferred form of the present invention, the blood bag system 60 is a closed system that enables substantially sterile sampling and limited sterile manipulation and access to the blood sample collected in the collection bag 62. A sterile docking device, such as a sterile port, may be used in place of the illustrated closed blood bag system. The specific size and configuration of the blood bag system will depend on variables readily controlled and discernible by one skilled in the art. The size of the box 40 and the size of the blood bag system 60 should correlate so that the type can be used in tandem forming the blood collection apparatus 40 of the present invention.

The invention is further described in the following non-limiting example.

EXEMPLIFICATION

Example 1

In one study, a total of 25 umbilical blood collection procedures were performed over a 9 month period on the placentas from infants born by caesarean section or vaginal birth. None of the birth events was preceded by prolonged rupture of membranes. The mean blood volume collected from each placenta in over 2 minutes was 65.6 cc, with a range of 30 cc to 110 cc.

Immediately after neonate delivery and umbilical cord separation, the placenta and umbilical stump were placed onto a sterile field for inspection and vessel access site determination. The inventive apparatus 40, described in detail above, was then implemented to obtain the blood sample.

The inventive apparatus 40 involves a sterile 100 cc polyvinyl chloride primary collection bag, available from Cutter Biological, Miles Inc., Berkeley, California, placed into an airtight acrylic vacuum chamber. An incoming phlebotomy line and an outgoing aliquot line extended from the collection bag through two ports 48, 48' in the gasketted top of the chamber 40.

The umbilical stump was prepared for phlebotomy with providing iodine and 70% isopropyl alcohol swabs. After the appropriate venous access site was identified, venipuncture was performed, using an integrally attached 16G needle, in the direction of the placenta. Suction was initiated to establish a negative pressure of approximately 5 mm Hg within the chamber. The suction source was a wall suction source, but other similar sources may be used as appropriate. The placental blood was thus drawn into the collection bag containing 14 ml of citrate-phosphate-dextrose-adenine (CPDA-1) anticoagulant. The collection bag was intermittently agitated during the collection period, which lasted up to approximately 2 minutes.

An average of 65.6 cc of blood can be collected in under two minutes. Adequate anticoagulation is achieved with 14 ml of anticoagulant pre-loaded in the primary collection bag 62 for blood volumes of over 65 cc. APTT values of over 90 seconds were observed for blood volumes in excess of 65 cc.

Upon completion of the phlebotomy, the vacuum was turned off and the phlebotomy needle and tubing were separated from the collection bag. The previously tared bag was then weighed and appropriately labelled. Surface cultures of the umbilical cord phlebotomy site were performed both prior to and following site preparation.

Surface cultures of the phlebotomy site demonstrate that sufficient decontamination is achieved following providing iodine and alcohol preparation. Additionally, no bacterial contamination was noted to occur in any of the 25 units throughout the 28 day storage period. Although these data suggest that umbilical blood phlebotomy can be performed safely and in aseptic fashion, the majority of placentas (21/25) were obtained following caesarean delivery without prolonged rupture of membranes.

To avoid contamination when removing blood aliquots from the primary bag 62 for either testing or potential transfusion, an integrally attached system of 6 satellite bags 72 was devised. The six branching satellite bags 72, each of up to 20 ml volume, are filled sequentially from the main bag and are heat sealed off. Each bag 72 may be used for up to 24 hours, during which time aliquots are removed by needle and syringe through an injection port. The blood units were stored at 4° C. and sampled weekly for four weeks.

Adequate anticoagulant (APTT over 90 seconds) on the day of collection was achieved in 15 specimens, all of the specimens having a blood volume of over 65 cc. Ten specimens, ranging in collected blood volumes of 65 cc to 110 cc, had mean APTT values of 65.3 (+/−10.2) seconds. APTT values for all 25 specimens at 1, 2, 3 and 4 weeks storage were over 90 seconds.

Surface cultures of the phlebotomy sites prior to preparation were positive for staphylococcus epidermidis in 2 of 25 samples. These two positive specimens represented blood collections from vaginally delivered placentas. However, all surface cultures taken after cord preparation, as well as blood cultures obtained weekly from stored units, remained negative.

Complete hematologic, blood chemistry and red cell viability data were collected on 16 umbilical blood phlebotomy samples, each stored over a four week period. Study samples were obtained on 0, 7, 14, 21 and 28 days of storage. Hematologic and viability data obtained using the inventive method and apparatus demonstrated no change in stored hematocrit values and low percentage hemolysis. Elevation in plasma potassium values was similar to that found in stored CPDA-1 adult whole blood. Red cell ATP and 2, 3 DPG values were also similar to those reported for adult red cells stored in CPDA-1.

Results of hematology analysis are shown in the following Table 1:

TABLE I

| | HEMATOLOGIC DATA | | |
|---|---|---|---|
| Days | Spun HCT (%) | WBC ($\times 10^9/l$) | Platelet counts ($\times 10^9/l$) |
| 0 | 42.06 ± 2.46 | 12.32 ± 4.68 | 272 ± 55 |
| 7 | 44.90 ± 2.67 | 10.52 ± 5.62 | 250 ± 68 |
| 14 | 42.96 ± 3.09 | 7.58 ± 2.50 | 238 ± 59 |
| 21 | 41.06 ± 1.08 | 6.63 ± 2.74 | 199 ± 51 |
| 28 | 41.32 ± 2.70 | 5.43 ± 1.84 | 161 ± 47 |

As shown in Table I, no significant change (42.6±2.46% on day 0, 41.32±2.7% on day 28) was seen in hematocrit values of the stored units over the four week storage period. No change in red cell morphology, determined as percent echinocytes on blood smear evaluation, was observed. Percent echinocytes during the four week period were 3±1%. White blood cell and platelet counts both decreased during the storage period. Interestingly, the platelet count was noted to be in excess of $161 \pm 47 \times 10^9/1$ with preserved morphology after 28 days of storage, however no platelet function studies were performed.

The following Table II shows the results of further chemical analysis:

TABLE II

| | BLOOD CHEMISTRY DATA | | |
|---|---|---|---|
| Days | Glucose (mmol/l) | Potassium (mmol/l) | pH |
| 0 | 29.1 ± 3.7 | 8.15 ± 3.40 | 6.85 ± 0.14 |
| 7 | 27.3 ± 4.2 | 19.21 ± 5.96 | 6.72 ± 0.12 |
| 14 | 23.7 ± 4.4 | 25.21 ± 5.12 | 6.67 ± 0.11 |
| 21 | 20.8 ± 36 | 28.38 ± 5.57 | 6.58 ± 0.09 |
| 28 | 18.4 ± 4.7 | 32.01 ± 5.94 | 6.51 ± 0.12 |

As shown in Table II, no significant changes were noted in plasma sodium, chloride, urea nitrogen, calcium, or lactate dehydrogenase values during the storage period. A fall in plasma glucose was accompanied by a fall in extracellular pH resulting from metabolic glycolysis by red cells during storage. Plasma pH never fell below 6.39. Extracellular potassium values rose to a maximal mean value of 32.01±5.94 mmol/1. The rise in potassium values exceed that expected based on percent hemolysis of the stored red cells.

The following Table III shows the results after blood cell viability analysis:

TABLE III

| | RED CELL VIABILITY | | |
|---|---|---|---|
| Days | Hemolysis (%) | ATP ($\mu$mol / g Hgb) | 2, 3 DPG ($\mu$mol / g Hgb) |
| 0 | 0.28 ± 0.07 | 4.32 ± 0.58 | 13.30 ± 1.00 |
| 7 | 0.32 ± 0.05 | 3.96 ± 0.36 | 6.68 ± 0.76 |
| 14 | 0.34 ± 0.05 | 4.00 ± 0.77 | 3.07 ± 1.10 |
| 21 | 0.36 ± 0.06 | 3.86 ± 0.79 | 2.03 ± 0.75 |
| 28 | 0.39 ± 0.05 | 3.46 ± 0.56 | 1.31 ± 0.28 |

Percent hemolysis of the stored red cell remained low during the four week period, reaching a maximum of 0.39±05% red cells hemolyzed following exposure to Drabkin's reagent. Intracellular ATP remained relatively stable, falling from 4.32±0.58 $\mu$mol/g Hgb on day 0 to 3.46±0.56 $\mu$mol/g Hgb on day 28. However, as expected, red cell 2,3-DPG concentration did fall precipitously to a low value of 1.31±0.28 $\mu$mol/g Hgb on 28.

Example 2

Cord blood is collected into the primary blood collection bag containing a sufficient amount of CPD anticoagulant to prevent coagulation of the collected blood. The phlebotomy vacuum chamber 40 described above is used at a negative pressure of approximately 30 mm Hg to 40 mm Hg. Collected blood volume is approximately 75-150 ml.

Approximately 5 ml of the collected cord blood is then transferred to a satellite transfer bag 72 for the following assays: complete blood count; differential; platelet count; Colony Forming Unit (CFU) Assay; flow cytometry studies for lymphocyte subsets and percentage progenitor cell (CD33, CD34) population; and HLA studies. DMSO is added to a final concentration of 10% by weight in the primary collection bag 62 utilizing an electronic pan scale. All superfluous tubing is heat sealed and detached. The cord blood cell suspension is then labelled and frozen utilizing a controlled rate freezer, and the sample is subsequently stored at −70° C.

The invention may be embodied in other specific forms without departing from the spirit or essential characteristics thereof. The present embodiments and examples are therefore to be considered in all respects as illustrative and not restrictive, the scope of the invention being indicated by the appended claims rather than by the foregoing description, and all changes that come within the meaning and range of equivalency of the claims are therefore intended to be embraced therein.

I claim:

1. A method for autologous blood transfusion into a neonate, comprising the sequential steps of:
   A. obtaining the placenta of said neonate;
   B. exposing an umbilical cord venous access site on said placenta;
   C. performing venipuncture at said venous access site using a cateter assembly, said assembly including a needle in communication with a blood collection bag having a predetermined amount of anticoagulant therein;
   D. applying a vacuum suction to said catether assembly so as to draw blood from said umbilical cord through said venous access site directly into said blood collection bag;
   E. intermittently agitating said collection bag while applying the vacuum suction during step (D);
   F. storing said blood collection bag containing said blood of step (D) for a selected amount of time; and
   G. transfusing said stored blood into said neonate.

2. The method of claim 1 wherein said vacuum suction is applied at a negative pressure of between about 5 mm Hg and 40 mm Hg.

3. Apparatus for collecting blood from a placenta for autologous neonate blood transfusion, comprising in combination:
   A. a substantially hollow box having a hinged sealable top panel, suction means integral with a bottom panel for applying a vacuum suction to the interior of said box, and a plurality of tubing ports;
   B. a blood bag assembly including:
      at least one primary flexible blood collection bag that collects blood drawn from said placenta as said vacuum suction is applied by said suction means, and
      a plurality of tubing elements extending from said bag and through said tubing ports in said box.

4. Apparatus of claim 3 wherein said primary blood bag contains a predetermined amount of an anticoagulant.

5. Apparatus of claim 3 further comprising at least one satellite bag in communication with said primary bag for selectively removing a blood sample from said primary bag.

6. Apparatus of claim 5 further comprising at least one auxiliary bag having a predetermined amount of a reagent.

7. A method for neonate autologous blood transfusion, comprising the steps of:
   A. obtaining the placenta associated with said neonate;
   B. exposing an umbilical cord venous access site on said placenta;
   C. collecting an amount of blood from said placenta at said access site into a flexible blood bag contained within a substantially hollow box by applying a vacuum suction to the interior of the hollow box;
   D. storing said collected amount of blood for a selected amount of time; and
   E. transfusing said stored collected blood of step D. into said neonate.

* * * * *

UNITED STATES PATENT AND TRADEMARK OFFICE
CERTIFICATE OF CORRECTION

PATENT NO. : 5,356,373
DATED : October 18, 1994
INVENTOR(S) : Robert A. Dracker It is certified that error appears in the above-identified patent and that said Letters Patent is hereby corrected as shown below:

On the title page:
The assignee should be corrected from "Miles Inc., Berkeley, California" to --The Research Foundation of State University of New York, Albany, New York--.

Signed and Sealed this

Twenty-first Day of March, 1995

*Attest:*

BRUCE LEHMAN

*Attesting Officer*    Commissioner of Patents and Trademarks